United States Patent
Kock et al.

(10) Patent No.: US 6,295,985 B1
(45) Date of Patent: Oct. 2, 2001

(54) ANAESTHETIC MACHINE

(75) Inventors: Mikael Kock, Akersberga; Pär Emtell, Vällingby, both of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/413,780

(22) Filed: Oct. 7, 1999

(30) Foreign Application Priority Data

Oct. 27, 1998 (SE) .................................................... 9803684

(51) Int. Cl.$^7$ ................................................. A61M 15/00
(52) U.S. Cl. ................................ 128/203.12; 128/203.14; 128/203.25
(58) Field of Search .................... 128/203.12, 203.14, 128/203.25

(56) References Cited

U.S. PATENT DOCUMENTS

| | | | |
|---|---|---|---|
| 1,567,868 | * 8/1925 | Schroder | 128/203.12 |
| 4,127,121 | * 11/1978 | Westenskow et al. | 128/203.14 |
| 4,224,940 | 9/1980 | Monnier | 128/205.16 |
| 4,259,303 | * 3/1981 | Nakaji et al. | 128/203.25 |
| 5,237,990 | * 8/1993 | Psaros et al. | 128/203.12 |
| 5,253,640 | * 10/1993 | Falb et al. | 128/203.12 |
| 5,320,093 | * 6/1994 | Raemer | 128/203.12 |
| 5,398,675 | * 3/1995 | Henkin et al. | 128/203.12 |
| 5,509,406 | * 4/1996 | Kock et al. | 128/203.14 |
| 5,515,845 | * 5/1996 | Filipovic et al. | 128/203.12 |
| 5,537,992 | * 7/1996 | Bjoernstijerna et al. | 128/203.14 |
| 5,678,537 | * 10/1997 | Bathe et al. | 128/203.12 |
| 5,699,788 | * 12/1997 | Lekholm et al. | 128/203.12 |
| 5,701,888 | * 12/1997 | Tham et al. | 128/203.12 |
| 5,730,119 | * 3/1998 | Lekholm | 128/203.25 |
| 5,806,513 | * 9/1998 | Tham et al. | 128/203.14 |

FOREIGN PATENT DOCUMENTS

| | | |
|---|---|---|
| 25 43 266 | 4/1977 | (DE) . |
| 0 121 255 | 10/1984 | (EP) . |
| 0 164 500 | 3/1985 | (EP) . |
| 0 284 227 | 9/1988 | (EP) . |
| 0 700 689 | 3/1996 | (EP) . |
| 0 813 883 | 12/1997 | (EP) . |
| 0 862 922 | 9/1998 | (EP) . |
| WO 96/36385 | 11/1996 | (WO) . |
| WO 97/19719 | 6/1997 | (WO) . |

* cited by examiner

*Primary Examiner*—Aaron J. Lewis
(74) *Attorney, Agent, or Firm*—Schiff Hardin & Waite

(57) ABSTRACT

An anaesthetic machine for connection to a patient's airways has a fan with an inlet and an outlet, a first system of flow paths connected between the fan's outlet and inlet, and a second system of flow paths connected between the fan's outlet and inlet. A fast system with wide variability with respect to operating modes is achieved by arranging a shunt valve at the fan's outlet in order to regulate the amount of gas flowing into the first system of flow paths and the second system of flow paths respectively, and a control unit is provided to control the shunt valve.

8 Claims, 1 Drawing Sheet

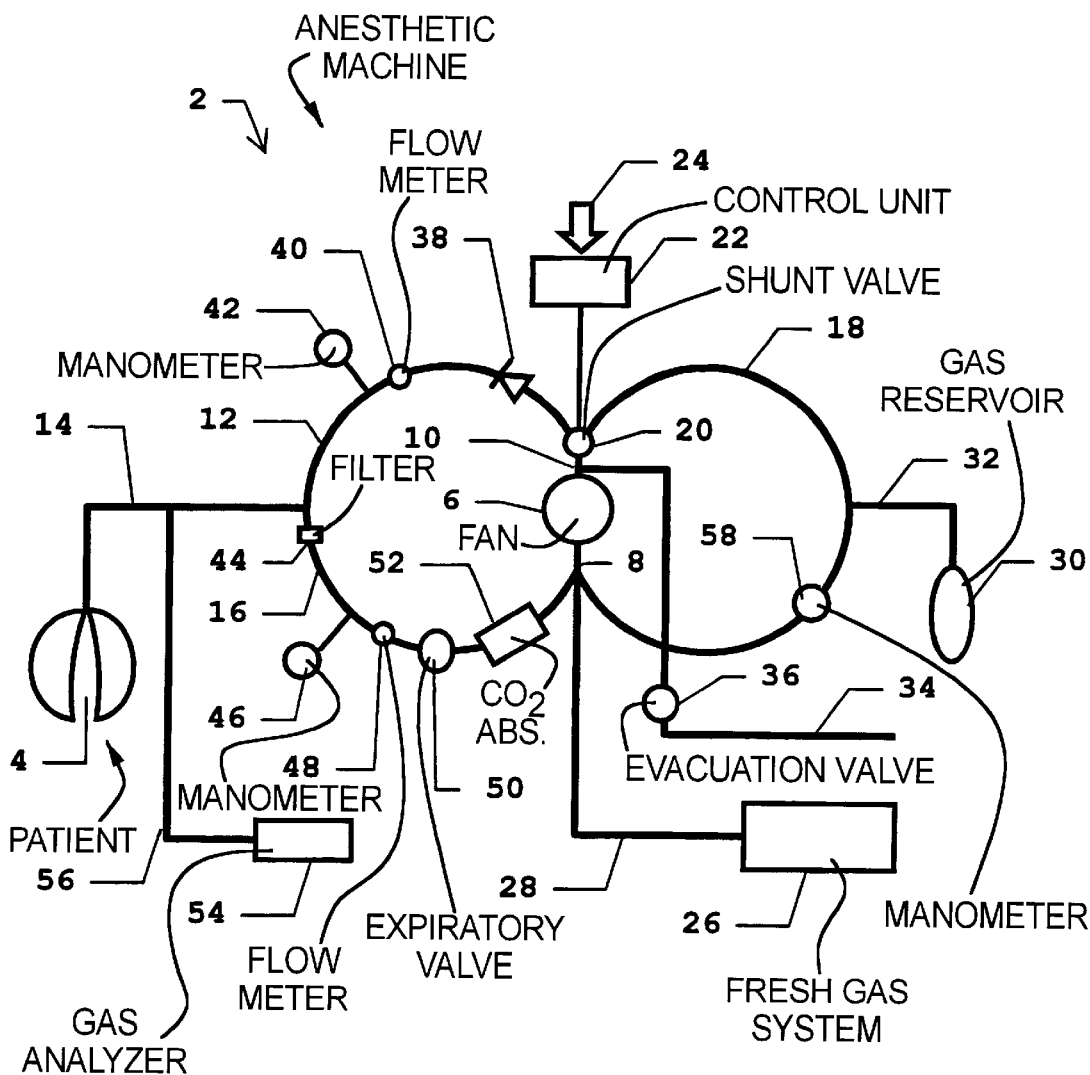

ANAESTHETIC MACHINE

BACKGROUND OF THE INVENTION

1. Field of the Invention

The present invention is directed to an anaesthetic machine for delivering anaesthetic to the airways of a patient, the anaesthetic machine being of the type having a gas flow generator with an inlet and an outlet, and a first system of flow paths connected between this inlet and outlet and a second system of flow paths also connected between this inlet and outlet.

2. Description of the Prior Art

Anaesthetic machines are usually based on a circular (loop) system in which breathing gas is returned to the patient after exhalation. The main reason for this is to minimize the consumption of expensive anaesthetic. Breathing gas is purified in a carbon dioxide absorber. Breathing can either be spontaneous or maintained with gas delivered to the patient in pulses. The pulses are usually generated by a bellows or piston. This kind of anaesthetic machine is usually referred to as a low-flow system. This is because a volume of gas, less than the total volume of gas in the circle system, usually passes every point in the flow paths in every breathing cycle.

European Application 164 500 describes another type of anaesthetic machine. This known anaesthetic machine has a fan to which a first system of flow paths and a second system of flow paths are connected. The first system includes an inspiratory line, a positive pressure reservoir, an inspiratory valve, an expiratory line, a negative pressure reservoir and an expiratory valve. The second system includes a return line between the fan's inlet and outlet and a pressure-controlled valve. A predetermined pressure gradient can be generated by the fan and maintained between the inspiratory section and the expiratory section of the first system. By regulating the inspiratory valve and expiratory valve, the breathing of a patient connected to the known anaesthetic machine can be controlled. If pressure in the expiratory section drops too far, the pressure-controlled valve opens, enabling gas to flow from the inspiratory section to the expiratory section via the second system.

This known anaesthetic machine has a number of disadvantages. For example, it does not allow the patient to breathe spontaneously, since breathing is completely controlled by the inspiratory and expiratory valves. Moreover, this known anaesthetic machine cannot provide all the various kinds of controlled breathing modes. As a result, this known anaesthetic machine has a limited range of use in practice.

European Application 813 883 describes a ventilator, such as one intended for respiratory care in the patient's home. In one embodiment, the ventilator has a gas reservoir with an inlet open to ambient atmosphere, a compressor for generating a flow of gas, a flow splitter that conducts gas, via an inspiratory tube, to a patient or, via a return tube, back to the gas reservoir. Oxygen can be dispensed into the return tube to raise the level of oxygen in the breathing gas.

This known ventilator, however, is not suitable for anaesthesia, mainly because it is open to atmosphere.

SUMMARY OF THE INVENTION

An object of the present invention is to provide an anaesthetic machine that overcomes the aforementioned problems associated with known anaesthetic machine.

The above object is achieved in accordance with the principles of the present invention in an anaesthetic machine having a gas flow generator with an inlet and an outlet and first and second flow path systems connected between the inlet and the outlet, a shunt valve connected at the outlet of the gas flow generator for regulating respective amounts of gas flowing in the first and second systems of flow paths, and a control unit which controls the shunt valve to control the degree of division of the respective amounts flowing into the first and second systems of flow paths.

A number of advantages are achieved when a shunt valve is arranged at a gas flow generator's outlet in order to regulate the amount of gas flowing into the first system of flow paths and the second system of flow paths respectively.

One advantage is that all types of breathing modes can be accommodated, both controlled and assisted breathing. The shunt valve regulates the exact amount of gas needed for the prevailing breathing mode. When a bias flow is allowed to be supplied to the patient, triggering can be obtained for spontaneous breathing.

The patient's expiration is facilitated in an embodiment wherein the fan actively draws gas through the expiratory section of the first system of flow paths. As a result, any carbon dioxide absorber in the system does not pose any resistance to expiration. Filters also can be used in a way that is impossible in low-flow anaesthetic systems.

Another advantage is that gas in the anaesthetic machine can be quickly replaced with a new gas. This is important in the switch to another anaesthetic agent and when the patient is to be awakened from anaesthesia. Gas in the system is appropriately evacuated through an evacuation line. This prevents anaesthetic gas from escaping into the air around the anaesthetic machine.

As used herein, "shunt valve" means any individual component or combination of components that is capable of splitting (in analog or discrete steps) a gas flow into at least two sub-flows.

As used herein, "gas flow generator" means an individual component or combination of components that is capable of generating a flow of gas. Fans, compressors and pumps in particular are examples of such a "gas flow generator."

In an embodiment wherein a gas reservoir is arranged in the flow paths, gas mixing is improved and made more homogenous in the whole system. The gas reservoir can be a hand ventilator for manual ventilation of the patient.

In another embodiment, the expiratory valve is arranged in the expiratory section of the first system of flow paths. The entire course of respiration can alternatively be regulated by the expiratory valve alone.

DESCRIPTION OF THE DRAWINGS

The single FIGURE is a schematic illustration of an embodiment of the anaesthetic machine according to the invention.

DESCRIPTION OF THE PREFERRED EMBODIMENTS

An embodiment of the anaesthetic machine 2 according to the invention is shown in the FIGURE. The anaesthetic machine 2 is only schematically depicted in the FIGURE. Individual components in the system are well known.

The anaesthetic machine 2 is connected to a patient 4 in order to supply her/him with a breathing gas during anaesthesia.

The anaesthetic machine 2 contains a fan 6 devised to generate a constant flow of gas. The magnitude of the flow must be sufficient to meet the needs of the patient 4. Larger flows' are also possible. For example, the flow can be so large that the same flow passes the fan several times during each breathing cycle. The advantages of this are described below in greater detail.

The fan 6 has an inlet 8 and an outlet 10. A first system of flow paths, including an inspiratory line 12, a patient line 14 and an expiratory line 16, proceeds from the outlet 10. The expiratory line 16 is connected to the inlet 8 of the fan 6. A second system of flow paths, including a return line 18 connected to the inlet 8, also proceeds from the outlet 10.

A shunt valve 20 is arranged at the outlet 10. The shunt valve 20 distributes the flow from the fan 6 into the two systems of flow paths. The reason for this is described below. A control unit 22 controls the shunt valve 20. Here, the control unit 22 controls the shunt valve 20 according to a number of input signals, schematically depicted with the arrow 24.

A fresh gas system 26 for preparing fresh breathing gas is connected to the inlet 8 by a fresh gas line 28. A gas reservoir 30 is connected to the return line 18 by the line 32. An evacuation line 34 connects the outlet 10 to a gas evacuation unit. An evacuation valve 36 opens when gas is evacuated from the systems of flow paths.

A number of components are arranged in the first system of 20 flow paths. A check valve 38, a flow meter 40 and a manometer 42 are arranged in the inspiratory line 12. A filter 44, a second manometer 46, a second flow meter 48, an expiratory valve 50 and a carbon dioxide absorber 52 are arranged in the expiratory line 16. A gas analyzer 54 for taking gas samples from a sampling tube 56 is connected to the patient line 14.

A third manometer 58 is arranged in the second system of flow paths.

The anaesthetic machine 2 can operate in a number of different ways for providing the patient 4 with the best possible breathing assistance during anaesthesia. In principle, the first system of flow paths functions in the same way as an intensive care system with all its different operating modes.

Before and after anaesthesia itself, the anaesthetic machine 2 can appropriately operate as an open system. During inspiration, the expiratory valve 50 is then kept closed. The fan 6 preferably generates a constant, large flow. Gas to the fan 6 is supplied from the gas reservoir 30 or the fresh gas system 26. The flow must at least correspond to the inspiratory flow needed by the patient 4. A controlled amount of the breathing gas is sent to the inspiratory line 10, via the shunt valve 20, from the outlet 10 of the fan 6. The diverted breathing gas is then carried to the patient 4 via the inspiratory line 12 and the patient line 14.

When pressure in the first manometer 42 and flow in the first flow meter 40 are measured, the control unit 22 is able to operate the shunt valve 20 very accurately, enabling the patient 4 to receive a specific volume of breathing gas or a specific pressure. In spontaneous breathing, it is the patient who regulates the main parameters. In supported or controlled breathing, the parameters are regulated according to the respiratory settings programmed by physician.

Gas which is not fed into the inspiratory line 12 is carried to the return line 18, back to the inlet 8 of the fan 6.

The expiratory valve 50 and the evacuation valve 36 open during expiration. The fan 6 continues to generate the same gas flow. Expired gas is then passed, via the patient line 14 and expiratory line 16, through the fan 6 and out into the evacuation line 34. The expiratory course can be regulated with the expiratory valve 50 according to the pressure measured by the second manometer 46 and flow measured by the second flow meter 48. Tn the final phase of expiration, a bias flow can be sent to the inspiratory line 12 via the shunt valve 20. This bias flow facilitates triggering of the patient's next breath in a known fashion.

It should be noted that the anaesthetic machine 2 also is able to operate as a closed system before and after anaesthesia. The carbon dioxide absorber 52 then absorbs any carbon dioxide in the expiratory air.

When anaesthetic gas is fed into the system via the fresh gas system 26 and the fresh gas line 28, the anaesthetic machine 2 switches primarily to closed system operation. This is to minimize consumption of expensive anaesthetic.

When the patient 4 is breathing spontaneously, it is sufficient for the control unit 22 to cause the shunt valve 20 divert a sufficient amount of breathing gas to the inspiratory line 12. The remaining breathing gas then circulates via the return line 18 back to the inlet 8. Carbon dioxide is removed from expired breathing gas in the carbon dioxide absorber 52.

When the patient 4 requires active breathing assistance, the same procedure can be used as described above except that the evacuation valve 36 is not activated to evacuate breathing gas.

Alternatively, a physician can manually provide breathing support. The gas reservoir 30 is designed to be an active part of the second system of flow paths. It can be constantly connected to the return line 18 or optionally connectable to same. It is then important for circulating breathing gas to be carried via the return line 18 to the gas reservoir 30 through a first channel in the line 32 (not shown in the FIGURE) and back to the return line 18 through a second channel in the line 32 (not shown in the FIGURE), i.e., all gas passes through the gas reservoir 30. A physician is then able to control the breathing of the patient 4 by manually squeezing the gas reservoir 30, thereby increasing pressure in the systems of flow paths.

Since some gas is absorbed by both the carbon dioxide absorber 52 and the body of the patient, supplementary gas is needed from the fresh gas system 26. Ideally only a supplement corresponding to consumption will be needed. In reality, more fresh gas is supplied than necessary. The surplus is removed via the evacuation line 34. The evacuation valve 36 then serves as a pressure relief valve.

The composition of the breathing gas can be monitored with the analyzer 54. Analysis results can be used both for monitoring and for controlling the composition of the fresh gas.

The fact that the fan 6 is able to generate a relatively' large, continuous flow of breathing gas, as noted above, produces several advantages. Gas in the system can then be forced to pass the carbon dioxide absorber 52 more often than in known anaesthesia systems (especially when the carbon dioxide absorber 52 is located in the return line 18). This results in more effective purification of the breathing gas. Gas in the system can be evacuated more rapidly than in other known anaesthesia systems. This makes it easier to switch to another anaesthetic during anaesthesia and supply the patient 4 more rapidly with anaesthetic-free gas after anaesthesia. A more homogenous gas mixture is achieved as a result of the large flow, especially when the gas reservoir 30 is also used.

The fan 6 also contributes to an effective reduction in the resistance exhalation poses to the patient 4. It particularly compensates for the carbon dioxide absorber 52 and any filters 44 in the expiratory line 16.

The generation of a continuous flow by the fan 6, however, is not essential to the operation of the anaesthetic machine 2.

The evacuation valve 26 can alternatively be arranged right next to the outlet 10 in series with the shunt valve 20. As already noted, the carbon dioxide absorber 52 can be located in the return line 18 instead of in the expiratory line 16. The carbon dioxide absorber 52, like e.g. the fresh gas connection, evacuation and expiratory valve, can otherwise be placed at a number of locations in the two systems of flow paths.

Additional components also can be connected to the anaesthetic machine. For example, a check valve can be placed in the expiratory line (check valve operation can be incorporated into the valves when the shunt valve and expiratory valve are membrane (flap) valves).

Distinguishing features of the anaesthetic machine according to the invention and prerequisites for its performance and function are the use of two systems of flow paths, a gas flow-generator and a shunt valve for controllable regulation of the amount of gas in the respective system of flow paths. Selection of the number of other components in the anaesthetic machine and their respective locations, however, depend to a large degree on the designer's perception of the best locations and relevant government stipulations as to specific locations for safety reasons.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anaesthetic machine comprising:

a gas flow generator having an inlet and an outlet;

a first system of flow paths connected between said outlet and said inlet, and adapted for connection to airways of a subject;

a second system of flow paths connected between said outlet and said inlet;

a source of anaesthetic communicating at least with said first system of flow paths;

a shunt valve connected at said outlet of said gas flow generator for regulating an amount of gas flowing into said first system of flow paths and into said second system of flow paths, respectively; and a control unit connected to said shunt valve for controlling a degree of division of said amount of gas into said first system of flow paths and into said second system of flow paths, respectively.

2. An anaesthetic machine as claimed in claim 1 wherein said gas flow generator is a gas flow generator which generates a predetermined flow of gas.

3. An anaesthetic machine as claimed in claim 1 further comprising a gas reservoir connected to said second system of flow paths.

4. An anaesthetic machine as claimed in claim 3 wherein said gas reservoir comprises a hand ventilator.

5. An anaesthetic machine as claimed in claim 1 further comprising a gas evacuation line connected to said outlet of said gas flow generator.

6. An anaesthetic machine as claimed in claim 1 wherein said source of anaesthetic is connected to said inlet of said gas flow generator.

7. An anaesthetic machine as claimed in claim 1 wherein said first system of flow paths comprises an inspiratory line and an expiratory line.

8. An anaesthetic machine as claimed in claim 1 further comprising an expiratory valve connected in said expiratory line.

* * * * *